United States Patent [19]

Williams et al.

[11] Patent Number: 4,767,414
[45] Date of Patent: Aug. 30, 1988

[54] IONIZING PLASMA LUBRICANT METHOD

[75] Inventors: Joel L. Williams, Cary; David A. Martin, Raleigh; David B. Montgomery, Cary, all of N.C.

[73] Assignee: Becton, Dickinson and Company, Franklin Lakes, N.J.

[21] Appl. No.: 36,733

[22] Filed: Apr. 10, 1987

Related U.S. Application Data

[63] Continuation of Ser. No. 734,438, May 16, 1985.

[51] Int. Cl.$^4$ ............................................. A61M 5/315
[52] U.S. Cl. ..................................................... 604/230
[58] Field of Search ................. 604/230, 263; 361/225, 361/226, 230; 204/164, 169

[56] References Cited

U.S. PATENT DOCUMENTS

| | | | |
|---|---|---|---|
| 4,072,769 | 2/1978 | Lidel | 204/164 |
| 4,188,426 | 2/1980 | Auerbach | 204/169 |
| 4,364,970 | 12/1982 | Imada et al. | 204/169 |

FOREIGN PATENT DOCUMENTS

| | | | |
|---|---|---|---|
| 0089124 | 9/1983 | European Pat. Off. | 204/164 |
| 0052889 | 4/1979 | Japan | 604/230 |
| 2054612 | 2/1981 | United Kingdom | 204/169 |

Primary Examiner—C. Fred Rosenbaum
Assistant Examiner—Mark F. Colosimo
Attorney, Agent, or Firm—Richard E. Brown

[57] ABSTRACT

A method to reduce high breakout and sustaining forces between slidable surfaces includes applying a film of lubricant to at least one of the surfaces and subjecting the lubricant and surface to an ionizing plasma. The invention includes articles having slidable surfaces of low breakout and sustaining forces.

9 Claims, 1 Drawing Sheet

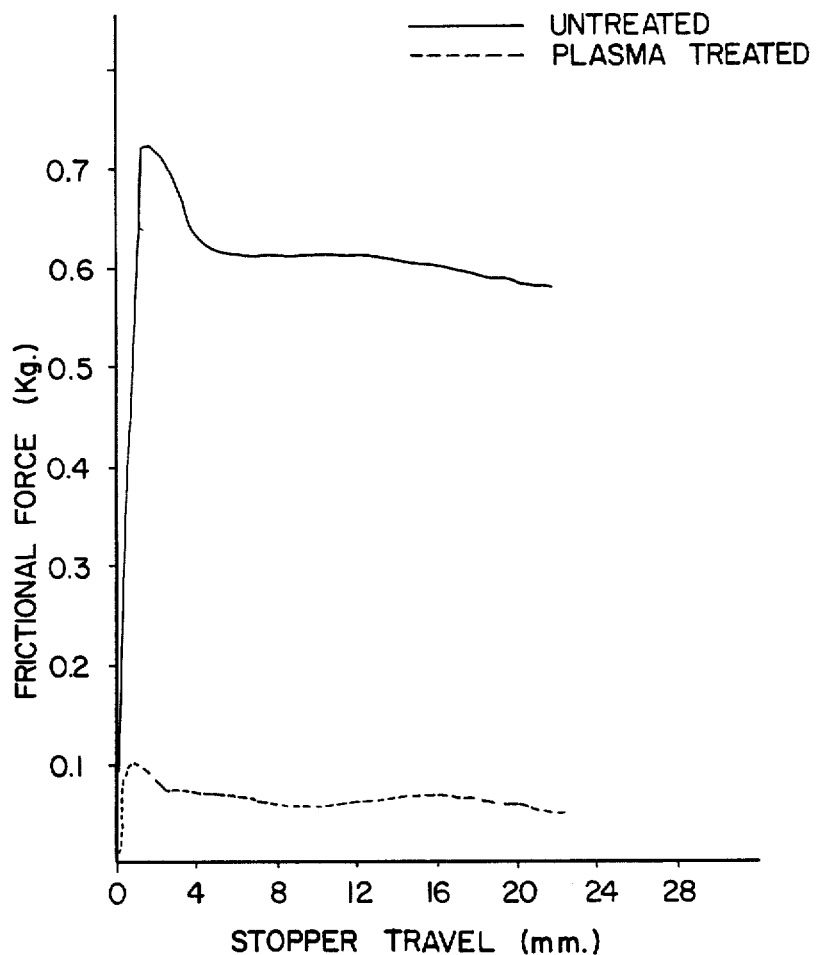

IONIZING PLASMA LUBRICANT METHOD

This is a continuation of application Ser. No. 734,438, filed May 16, 1985.

BACKGROUND OF THE INVENTION

1. Field of the Invention

This invention relates to a method to reduce static and kinetic friction between slidable surfaces, and to articles of low friction prepared thereby.

2. Description of the Prior Art

Certain devices require slow and controlled initiation and maintenance of sliding movement of one surface over another surface. It is well known that two stationary surfaces having a sliding relationsip often exhibit sufficient resistance to initiation of movement that gradually increased pressure applied to one of the surfaces does not cause movement until a threshold pressure is reached at which point a sudden sliding separation of the surfaces takes place. This sudden separation of stationary surfaces into a sliding relationship is herein referred to as breakout.

Breakout is particularly troublesome in liquid dispensing devices, such as syringes, used to deliver small, accurately measured quantities of a liquid by smooth incremental line to line advancement of one surface over a graduated second surface. The problem is also encountered in devices using stopcocks, such as burets, pipets, addition funnels and the like where careful dropwise control of flow is desired.

The problem of breakout is related to friction. Friction is generally defined as the resisting force that arises when a surface of one substance slides, or tends to slide, over an adjoining surface of itself or another substance. Between surfaces of solids in contact, there may be two kinds of friction: (1) the resistance opposing the force required to start to move one surface over another, conventionally known as static friction, and (2) the resistance opposing the force required to move one surface over another at a variable, fixed, or predetermined speed, conventionally known as kinetic friction.

The force required to overcome static friction and induce breakout is referred to as the breakout force, and the force required to maintain steady slide of one surface over another after breakout is referred to as the sustaining force. Two main factors contribute to static friction and thus to the breakout force. The term "stick" as used herein denotes the tendency of two surfaces in stationary contact to develop a degree of adherence to each other. The term "inertia" is conventionally defined as the indisposition to motion which must be overcome to set a mass in motion. In the context of the present invention, inertia is understood to denote that component of the breakout force which does not involve adherence.

Breakout force, in particular the degree of stick, varies according to the composition of the surfaces. In general, materials having elasticity show greater stick than non-elastic materials, particularly when the surfaces are of dissimilar composition. The length of time that surfaces have been in stationary contact with each other also influences breakout force. In the syringe art, the term "parking" denotes storage time, shelf time, or the interval between filling and discharge. Parking generally increases breakout force, particularly if the syringe has been refrigerated during parking.

A conventional approach to overcoming breakout has been application of a lubricant to a surface to surface interface. Common lubricants used are hydrocarbon oils, such as mineral oils, peanut oil, vegetable oils and the like. Such products have the disadvantage of being soluble in a variety of fluids, such as vehicles commonly used to dispense medicaments. In addition, these lubricants are subject to air oxidation resulting in viscosity changes and objectionable color development. Further, they are particularly likely to migrate from the surface to surface interface. Such lubricant migration is generally thought to be responsible for the increase in breakout force with time in parking.

Silicone oils are also commonly used as lubricants. They are poor solvents and are not subject to oxidation, but migration and stick do occur, and high breakout forces are a problem.

Polytetrafluoroethylene surfaces provide some reduction in breakout forces, but this material is very expensive, and the approach has not been totally effective. Thus there is a need for a better method to overcome high breakout forces whereby smooth transition of two surfaces from stationary contact into sliding contact can be achieved.

Formation of an ionizing plasma by electromagnetic activation of a gas by either glow discharge or corona discharge and use of such a plasma for modification of a surface, in particular for deposition of a material onto a polymeric surface, are well known. Exemplary of such teachings are U.S. Pat. No. 4,364,970 to Imada et al. and U.S. Pat. No. 4,072,769 to Lidel.

SUMMARY OF THE INVENTION

One aspect of the present invention comprises a method to reduce the forces required for breakout of surfaces from stationary contact into sliding contact and to maintain the surfaces in sliding contact. At least one of a surface and a lubricant are treated with an ionizing plasma and the lubricant is applied to at least one of the surfaces prior to or subsequent to application of the plasma.

In a preferred embodiment of the invention, the lubricant is a low molecular weight silicone oil applied to at least one of the surfaces prior to the plasma treatment whereby both the silicone oil and the surface are subjected to the plasma. In the most preferred embodiment of the invention, the lubricant is a low molecular weight polydialkylsiloxane applied to the surfaces of a syringe barrel and associated syringe stopper prior to the plasma treatment.

Another aspect of the invention includes articles having slidable surfaces of low breakout and sustaining forces achieved substantially in accordance with the method of the invention.

In accordance with the method of the invention, the force required to achieve breakout is greatly reduced, whereby transition of surfaces from stationary contact to sliding contact occurs without a sudden surge. When breakout is complete and the surfaces are in sliding contact, they slide smoothly upon application of very low sustaining force. Substantially less lubricant is required and lubricant migration is eliminated. The effect achieved by the method of the invention is of long duration, and articles, such as syringes, retain the advantages of low breakout and sustaining forces throughout any parking period. When the surfaces are part of a liquid dispensing device, small highly accurate increments of liquid may be dispensed repeatedly without sudden surges. Thus, a syringe treated according to the method of the invention may be used to administer a medicament to a patient without the danger of surges whereby accurate control of dosage and greatly enhanced patient safety are realized.

BRIEF DESCRIPTION OF THE DRAWING

The FIGURE is a curve of breakout and sustaining forces for a syringe barrel lubricated with a silicone oil showing the effect of treatment with an ionizing plasma.

DETAILED DESCRIPTION OF THE INVENTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated. The scope of the invention will be measured by the appended claims and their equivalents.

In accordance with the method of the invention, surfaces which have a sliding relationship with each other are treated with a lubricant and subjected to an ionizing plasma, whereby breakout of the surfaces may be accomplished without application of high breakout force. The method of the invention may be applied to any surface which slides in contact with another surface. Materials from which the surfaces may be fabricated include glass, metal, ceramic, plastic, rubber and the like. The method is most effective and most useful for surfaces made of materials which have elasticity, as, for example, surfaces consisting of rubber or various polymers. Surfaces which are particularly responsive to the method of the invention are those fabricated from natural or synthetic rubbers or from thermoplastic or thermoset polymers such as polyethylene, polypropylene, polystyrene, polytetrafluoroethylene and the like.

A lubricant is applied to at least one of the surfaces such that, when the surfaces are in contact, the lubricant is situated at the interface of the surfaces. Suitable lubricants are hydrocarbon oils such as vegetable oil, peanut oil, mineral oil and the like, or, preferably, a synthetic oil such as a silicone. Any suitable silicone oil may be used, or, if desired, a mixture of oils may be used. Preferred silicone oils have molecular weights of from about 100 to 200,000, preferably from about 1,000 to 100,000. The most preferred class of lubricants are the polydialkylsiloxanes of general structure I:

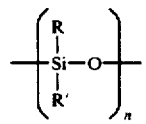

I wherein R and R' may be independently a lower alkyl of 1 to 20 carbon atoms, preferably 1 to 8 carbon atoms, and n may be an integer from 1 to 2000, preferably 1 to 800. The preferred lubricants of structure I have viscosities of from about 10-100,000, preferably about 50 to 1000 centistokes.

Application of a film of lubricant to the sliding surfaces may be accomplished by any suitable method, as, for example, dipping, brushing, spraying and the like. The lubricant may be applied neat or it may be applied in a solvent, and the solvent subsequently removed by evaporation. The lubricant film may be of any convenient thickness and, in practice, the thickness will be determined by such factors as the viscosity of the lubricant and the temperature of application. For reasons of economy, the film preferably is applied as thinly as practical, since no significant advantage is gained by thicker films.

The lubricant and surfaces may be separately treated with an ionizing plasma prior to application of the lubricant. Preferably, the lubricant is applied to the surface, and the surface and lubricant are treated together with the ionizing plasma whereby both the lubricant and the surface are subjected to the plasma. If desired, the surfaces, after lubrication, may be assembled into stationary contact prior to plasma treatment.

The plasma treatment may be carried out in any plasma generator, as, for example, those described in U.S. Pat. No. 3,847,652. Any suitable ionizing plasma may be used, as, for example, a plasma generated by a glow discharge or a corona discharge. The plasma may be generated from a variety of gases or mixtures thereof. Gases frequently used include air, hydrogen, helium, ammonia, nitrogen, oxygen, neon, argon, krypton and xenon. Any gas pressure may be used, however, gas pressures are advantageously maintained at 5 mm of Hg or below, preferably from about 0.1 to about 1.0 mm of Hg, in order to benefit from reduced voltage requirements.

A wide range of power settings, radio frequencies and durations of exposure of the lubricant and surface to the plasma may be used. Ranges for these three parameters which provide advantageous results are DC or AC power levels up to about 200 watts, from about 0.1 to about 50 megahertz and from about 0.1 to about 30 minutes, respectively. Preferred ranges are 10-50 watts, 10-20 megahertz and 2-10 minutes, respectively.

Breakout forces and sustaining forces may be conveniently measured on a universal mechanical tester or on a testing machine of the type having a constant rate of cross-head movement, as, for example an Instron model 1122. The FIGURE shows the breakout forces of a thermoplastic synthetic rubber syringe stopper in a syringe barrel and the sustaining forces required to move the stopper at a rate of 100 mm per minute after a park time of five minutes. The solid line shows these forces for an untreated syringe stopper and barrel lubricated with a silicone oil, and the dotted line shows the same forces measured after ionizing plasma treatment of the lubricated barrel. It is seen that the breakout and sustaining forces in the absence of plasma treatment are 0.72 and 0.61 kg respectively and that, after plasma treatment, these forces drop to 0.1 and 0.065 kg respectively. After breakout, these sustaining forces remain substantially constant regardless of the length of stopper travel.

It is believed, although as yet unsubstantiated, that the plasma treatment induces cross-linking in the silicone oil, whereby the lubricant is converted to a high molecular weight three dimensional polymer network. It is further believed that highly reactive species, most likely free radicals, are formed in the silicone polymer network and in the surfaces which react together to provide a degree of chemical bonding between the lubricant and the surfaces. In addition to bonding, it is postulated that the plasma treatment induces portions of the lubricant, most likely uncrosslinked ends, to enter openings generated in the surface by the plasma treatment whereby stability of the lubricant film and resistance to migration is enhanced.

In another aspect of the invention, articles having slidable surfaces with reduced breakout and sustaining forces are provided. Any article having suitable surfaces treated in accordance with the method of the invention is included within the scope of the invention. Exemplary of the articles included are syringes, syringes equipped with syringe pumps, and liquid dispensing or liquid metering devices, in particular those utilizing stopcocks for precision control of flow, such as pipets, burets, addition funnels and the like.

The following examples are provided to further describe the invention, but are not to be construed in any way as limitative of the invention.

EXAMPLE I

A film of 100 cS polydimethylsiloxane was wiped onto the contacting lip of a Kraton TM (Shell Corp. trade name for styrene-butadiene copolymer) stopper. After exposure to a nitrogen gas plasma for 5 minutes at a pressure of 250 mTorr and 50 watts power in an International Plasma Corp. (IPC) plasma generator, Model 2103-B, the stopper was assembled into an unlubricated 10 cc polypropylene syringe barrel. The breakout force was determined on an Instron model 1122 universal mechanical tester and found to be 500% lower than the breakout force of an untreated stopper measured under the same conditions.

EXAMPLE II

A film was applied to the inside surface of a 10 cc polypropylene syringe barrel by dipping the barrel into a 1.5% (weight/volume) solution of 100 cS polydimethylsiloxane in Freon TF TM (E. I. DuPont Co. trade name for dichlorodifluoromethane). The barrel was exposed to an air plasma for 10 minutes at 300 mTorr and 125 watts power in the IPC plasma generator. An unlubricated Kraton stopper was assembled into the syringe barrel and, after setting the assembly aside for 5 minutes, the breakout force was determined on the Instron and compared with the breakout force of an identical lubricated syringe and stopper assembly in the absence of plasma treatment. The results are depicted in the FIGURE and show breakout forces of 0.72 kg and 0.1 kg respectively for the untreated assembly and treated assembly respectively. The FIGURE also shows that the sustaining forces required to move the stopper at a rate of 100 mm per minute were 0.61 kg for the untreated assembly and 0.065 kg for the plasma treated assembly.

EXAMPLE III

The experiment of Example II was repeated except the syringe barrel was treated for 15 seconds with a corona induced plasma at a pressure of 20 Torr with a capacitively coupled, pulsed 150 kHz generator. Breakout force of the plasma treated assembly was reduced by 500% compared to an untreated assembly.

EXAMPLE IV

The experiment of Example III was repeated except 500 cS polymethyloctylsiloxane was used. Breakout force of the plasma treated assembly was reduced by 500% compared to an untreated assembly.

EXAMPLE V

The experiment of Example II was repeated except that a silicone blend consisting of 2 parts by volume of 10 cS polydimethylsiloxane and 1 part by volume of 12,500 cS polydimethylsiloxane was used. Breakout force of the plasma treated assembly was reduced by 500% compared to an untreated assembly.

Thus in accordance with the method of the invention, breakout forces between slidable surfaces are greatly reduced by plasma treatment of the surfaces and a lubricant for the surface to surface interface. Sudden breakout of the surfaces is avoided, and sliding of one surface over another, once initiated by breakout, may be maintained with reduced sustaining force. Articles of low breakout and sustaining forces prepared by the method of the invention are within the purview of the present invention.

What is claimed is:

1. An article having reduced breakout and sustaining forces comprising a plasma-treated surface, a second surface slidably engaged therewith and a plasma-treated lubricant at the interface of said surface.

2. The article of claim 1 wherein said second surface is a plasma-treated surface.

3. The article of claim 1 wherein said lubricant is silicone oil.

4. An article having reduced breakout and sustaining forces comprising at least two surfaces in a slidably engaging relationship and a plasma-treated lubricant at the interface of said surfaces.

5. The article of claim 4 wherein said lubricant is silicone oil.

6. The article of claim 1 which is a syringe.

7. The article of claim 4 which is a syringe.

8. The article of claim 1 wherein one of said surfaces is a surface of a stopcock.

9. The article of claim 4 wherein one of said surfaces is a surface of a stopcock.

* * * * *